United States Patent
Takama

(12) United States Patent    (10) Patent No.: US 8,687,863 B2
Takama    (45) Date of Patent: Apr. 1, 2014

(54) IMAGE PROCESSING APPARATUS, CONTROL METHOD THEREOF AND COMPUTER PROGRAM

(75) Inventor: Yasufumi Takama, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 194 days.

(21) Appl. No.: 13/130,319

(22) PCT Filed: Dec. 8, 2009

(86) PCT No.: PCT/JP2009/070795
§ 371 (c)(1),
(2), (4) Date: May 20, 2011

(87) PCT Pub. No.: WO2010/071091
PCT Pub. Date: Jun. 24, 2010

(65) Prior Publication Data
US 2011/0243408 A1    Oct. 6, 2011

(30) Foreign Application Priority Data
Dec. 19, 2008 (JP) ................................. 2008-324709

(51) Int. Cl.
*G06K 9/00* (2006.01)
(52) U.S. Cl.
USPC ............................... 382/128; 128/922; 378/4
(58) Field of Classification Search
USPC ................. 382/100, 128, 129, 130, 131, 132; 128/922; 378/4–27
See application file for complete search history.

(56) References Cited
U.S. PATENT DOCUMENTS

| | | | | |
|---|---|---|---|---|
| 4,423,931 A | * | 1/1984 | Shapiro | 351/206 |
| 5,029,220 A | * | 7/1991 | Juday | 382/128 |
| 5,220,360 A | * | 6/1993 | Verdooner et al. | 351/212 |
| 5,751,395 A | * | 5/1998 | Thall | 351/221 |
| 5,880,813 A | * | 3/1999 | Thall | 351/221 |
| 6,563,626 B1 | * | 5/2003 | Iwasaki | 359/292 |

(Continued)

FOREIGN PATENT DOCUMENTS

| | | |
|---|---|---|
| JP | 2007-117714 A | 5/2007 |
| JP | 2007-325831 A | 12/2007 |

(Continued)

OTHER PUBLICATIONS

International Search Report mailed Jan. 26, 2010, and discussed in the Written Opinion of the International Searching Authority completed Jan. 13, 2010, in International Application No. PCT/JP2009/070795.

(Continued)

*Primary Examiner* — Anand Bhatnagar
(74) *Attorney, Agent, or Firm* — Fitzpatrick, Cella, Harper & Scinto

(57) ABSTRACT

One aspect of embodiments of the present invention relates to an image processing apparatus which specifies one of boundary positions of retina layers in a fundus image showing a retina tomosynthesis, sets a distance transfer function for converting the distance from the specified boundary position to a parameter expressing opacity such that the peak position of the opacity is set to a predetermined position in the retina, sets a luminance transfer function for converting a luminance value of the fundus image to the parameter expressing opacity, and generates a translucent display image by calculating the opacity of respective positions of the tomosynthesis using the distance transfer function and the luminance transfer function, and by volume rendering.

44 Claims, 8 Drawing Sheets

(56) References Cited

U.S. PATENT DOCUMENTS

| | | | |
|---|---|---|---|
| 7,203,351 B1* | 4/2007 | Swindale et al. | 382/128 |
| 7,905,596 B2 | 3/2011 | Aoki et al. | |
| 8,098,278 B2 | 1/2012 | Yumikake et al. | |
| 8,118,752 B2* | 2/2012 | Hetling et al. | 600/558 |
| 8,170,293 B2* | 5/2012 | Tosa et al. | 382/117 |
| 8,223,143 B2* | 7/2012 | Dastmalchi et al. | 345/418 |
| 8,363,783 B2* | 1/2013 | Gertner et al. | 378/65 |
| 8,366,271 B2* | 2/2013 | Izatt et al. | 351/206 |
| 8,401,246 B2* | 3/2013 | Huang et al. | 382/117 |
| 2007/0070295 A1 | 3/2007 | Tsukada et al. | |
| 2007/0216909 A1* | 9/2007 | Everett et al. | 356/479 |
| 2007/0285619 A1 | 12/2007 | Aoki et al. | |
| 2010/0110375 A1 | 5/2010 | Nishio et al. | |
| 2010/0118132 A1 | 5/2010 | Yumikake et al. | |
| 2010/0189334 A1* | 7/2010 | Tomidokoro et al. | 382/131 |

FOREIGN PATENT DOCUMENTS

| | | |
|---|---|---|
| JP | 2008-006274 A | 1/2008 |
| JP | 2008-073099 A | 4/2008 |
| JP | 2008-267891 A | 11/2008 |
| JP | 2008-289642 A | 12/2008 |
| JP | 2008-295804 A | 12/2008 |
| JP | 2009-119107 A | 6/2009 |
| WO | 2008/146457 A1 | 12/2008 |

OTHER PUBLICATIONS

Elisa Ricci et al., Retinal Blood Vessel Segmentation Using Line Operators and Support Vector Classification, IEEE Transactions on Medical Imaging, vol. 26, No. 10, pp. 1357-1365, Oct. 2007.

Thomas Walter et al., A Contribution of Image Processing to the Diagnosis of Diabetic Retinopathy—Detection of Exudates in Color Fundus Images of the Human Retina, IEEE Transactions on Medical Imaging, vol. 21, No. 10, pp. 1236-1243, Oct. 2002.

Yonezawa et al. U.S. Appl. No. 13/050,287, filed Mar. 17, 2011.

* cited by examiner

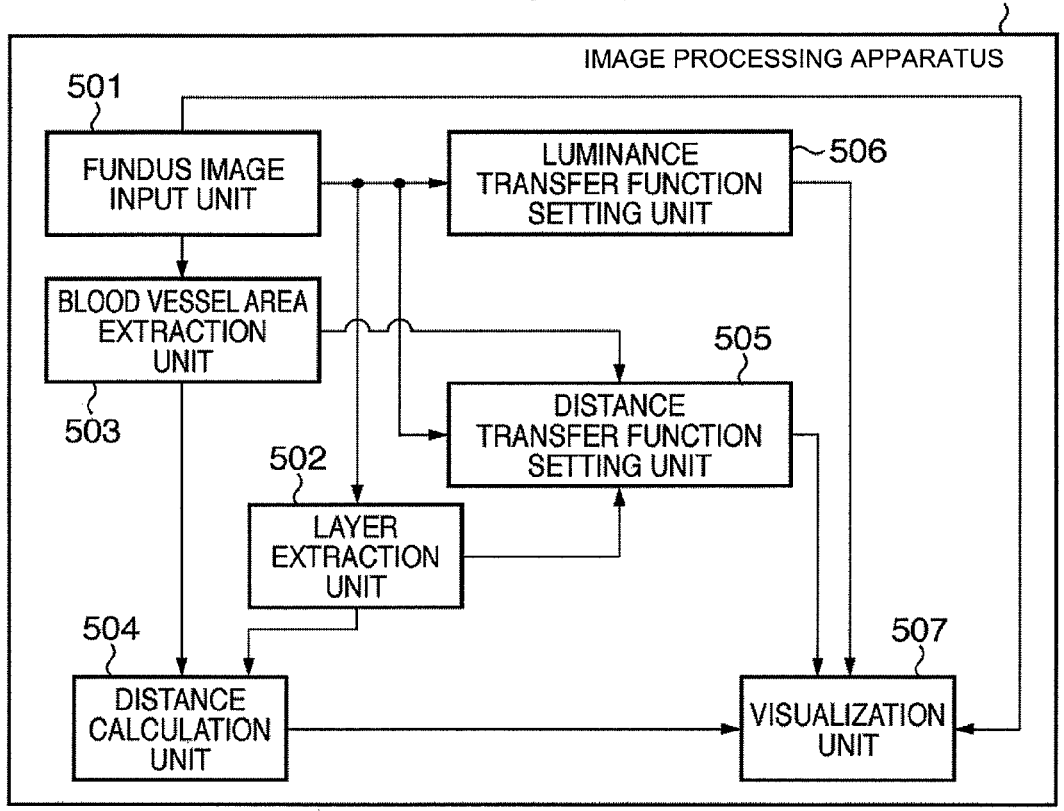

IMAGE PROCESSING APPARATUS, CONTROL METHOD THEREOF AND COMPUTER PROGRAM

TECHNICAL FIELD

The present invention relates generally to an image processing apparatus, a control method thereof and a computer program.

BACKGROUND ART

In ophthalmology, a fundus camera has generally been used to capture a picture of the fundus of the eye. In recent years, as an optical coherence tomography (hereinafter "OCT") has appeared, capturing tomosynthesis of a retina has become possible. As a result of this, new knowledge in ophthalmology that the retina forms a layer structure and that the layer structure is destroyed as disease progresses has been discovered. At present, as disclosed in the specification of Japanese Patent Laid Open No. 2008-073099, the layer structure is extracted from the retinal volume data, which is reconstructed from plural tomosynthesis of the captured retina, and the information thereof is utilized in the diagnosis of eye disease. Hereinafter, the fundus picture and retinal volume data will be referred to the fundus image.

In the existing technology, optometrists read the image of the layer structure of the retina by using the tomosynthesis or volume data, or they read the image of the condition of a fundus blood vessel or achromoderma by using the fundus picture. The fundus blood vessel is the sole observable vessel from outside the body, and various indications or phenomena of the disease can be confirmed from the fundus blood vessel. Among them, the cross-section in which the blood vessel occupied by arterial sclerosis is enlarged and contacts the adjacent blood vessel is a known as the phenomenon that causes the blood vessel to burst and is possibly linked to blindness in the worst case. Therefore, it is meaningful for optometrists to understand the blood flow in the fundus blood vessel in order to diagnose anomalies. Further, it can be linked with early detection of the disease in patients and early recovery from or prevention of blindness. For such reasons, in the specification of Japanese Patent Laid Open No. 2007-325831, the method of extracting the two-dimensional blood vessel area from the accumulated image generated by accumulating the fundus image or luminance value in the depth direction is disclosed. Further, the method of extracting the blood vessel area or achromoderma area from the fundus picture is disclosed in Elisa Ricci, Renzo Perfetti, "Retinal Blood Vessel Segmentation Using Line Operators and Support Vector Classification, "IEEE Transactions on Medical Imaging, Vol. 26 No. 10, PP1357-1365, 2007 or Thomas Walter, Jean-Claude Klein, Pascale Messin and Ali Erginary: "A Contribution of Image Processing to the Diagnosis of Diabetic Retinopathy-Detection of Exudates in Color Fundus Image of the Human Retina, "IEEE Transactions on Medical Imaging, Vol. 21, No. 10, PP1236-PP1243, October 2002, respectively.

However, in the fundus picture, the flow in the fundus blood vessel can only be observed in two dimensions. Accordingly, three-dimensional overlap of the fundus blood vessel as seen in the cross-section cannot be observed. At present, when OCT appears and the retinal volume data can be reconstructed with high resolution from the tomosynthesis, the three-dimensional flow of the fundus blood vessel can be observed, and the cross-section can possibly be observed directly.

In order to observe the retinal volume data, a method called volume rendering in which the volume data is displayed to be translucent by converting the value owned by the voxel to opacity and color by the transfer function is effective. The transfer function governing clarity is expressed, for example, as shown in FIG. 1, as a function defining the luminance value in on horizontal axis and the opacity on the vertical axis. Generally, the user can manually set the shape of the transfer function, the position of the peak or the width of the peak using a user interface. Further, as shown in the specification of Japanese Patent Laid Open No. 2008-006274, an automatic design is possible such that the range of the CT value calculated from the average value and variance of the CT value histogram fitted by the Gaussian function is displayed to be opaque by using the fact that the CT value histogram of the internal organ or the blood vessel displayed on CT has a peak by each organ.

DISCLOSURE OF INVENTION

The following problems exist in the visualization of 3D flow of the blood in the fundus blood vessel by using the retinal volume data.

The method disclosed in the specification of Japanese Patent Laid Open No. 2007-325831 or the publication by Elisa Ricci, et al., is to extract the two-dimensional fundus picture or the accumulated image of the fundus blood vessel, and the three-dimensional position of the fundus blood vessel cannot be identified.

In the method according to the specification of Japanese Patent Laid Open No. 2008-006274, the blood vessel area in the luminance value histogram of OCT does not present the peak, so it is difficult to visualize the three-dimensional blood flow in the fundus blood vessel. Also, in the retinal tomosynthesis 201 as shown in FIG. 2, the area in the vicinity of the lower end of the nerve fiber layer where the fundus blood vessel 202 runs is an area of high luminance. Further, as the fundus blood vessel 202 strongly reflects light, the luminance value becomes high. That is, the area where the fundus blood vessel 202 runs has low contrast, and even if the transfer function is set manually based on the luminance value, it is difficult to visualize only the fundus blood vessel.

Accordingly, the present invention allows improvement over the problems encountered in the prior art described above and to provide the technology to visualize the three-dimensional flow in the blood vessel or three-dimensional distribution of the achromoderma from the retinal volume data.

One aspect of embodiments of the present invention relates to an image processing apparatus which specifies one of the boundary positions of retina layers in a fundus image showing a retina tomosynthesis, sets a distance transfer function for converting the distance from the specified boundary position to a parameter expressing opacity such that the peak position of the opacity is set to a predetermined position in the retina, sets a luminance transfer function for converting a luminance value of the fundus image to the parameter expressing opacity, and generates a translucent display image by calculating the opacity of respective positions of the tomosynthesis using the distance transfer function and the luminance transfer function, and by volume rendering.

Further features of the present invention will become apparent from the following description of exemplary embodiments with reference to the attached drawings.

BRIEF DESCRIPTION OF DRAWINGS

FIG. 5 is a chart showing a functional structure of the image processing apparatus 1 according to an embodiment of the present invention.

FIG. 6 is a chart showing one example of the functional structure of a blood vessel area extraction unit 503 according to an embodiment of the present invention.

DESCRIPTION OF THE EMBODIMENT

Embodiments of an image processing apparatus according to the present invention will be described in detail hereinafter with reference to the attached drawings. However, the scope of the invention is not restricted to the embodiments and the attached drawings.

First Embodiment

Visualization of a Blood Vessel Blood Vessel

Figure 3:
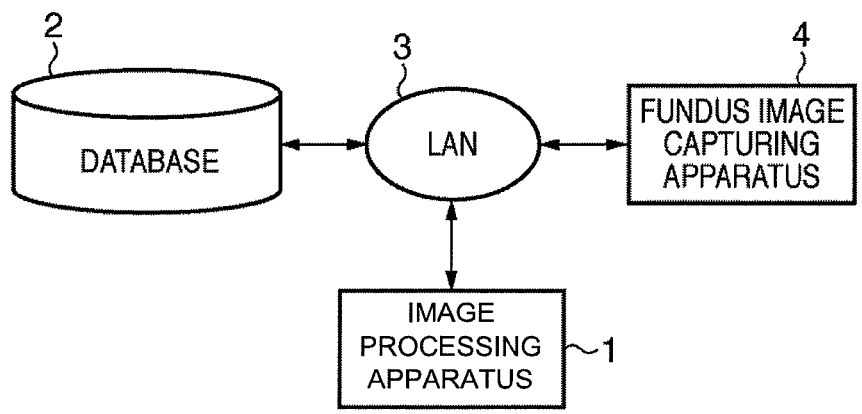
FIG. 3 is a chart showing one example of the structure of an image processing system according to an embodiment of the present invention.
Figure 4:
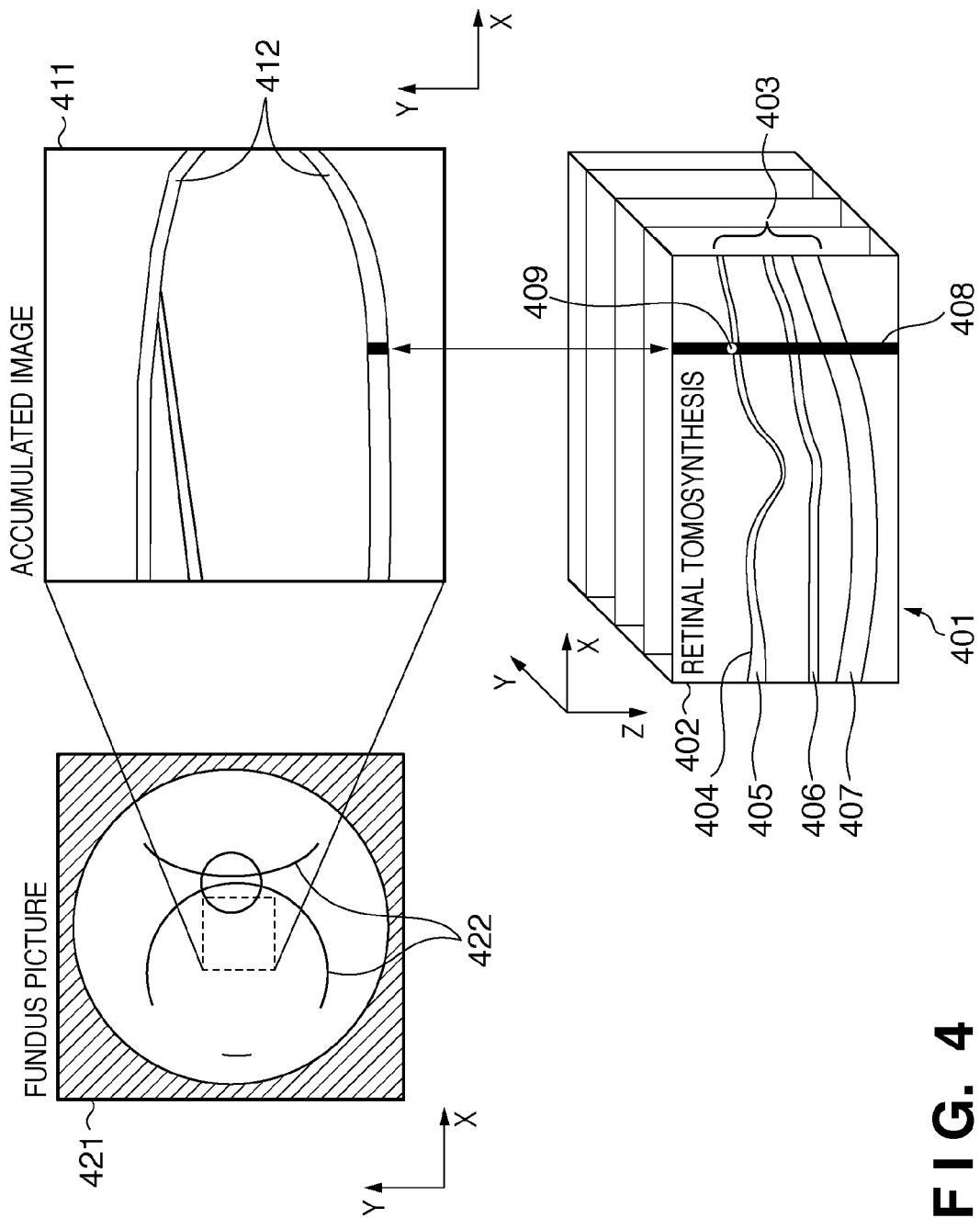
FIG. 4 is a chart for explaining the relationship of fundus picture, retinal volume data and accumulated image according to an embodiment of the present invention.

FIG. 3 is a chart showing one example of the structure of an image processing apparatus according to the present embodiment. In this embodiment, an image processing apparatus 1 reads out a fundus image from a database 2 through a LAN 3. Alternatively, a memory device such as an FDD, CD-RW drive, MO drive, or ZIP drive, or the like, may be connected to the image processing apparatus 1 and the fundus image may be read out from such a drive. In addition, a medical image or the like may be obtained directly from a fundus image capturing apparatus 4 via the LAN 3. In addition to the fundus image, the database 2 stores patient names or patient data, thickness information of a retina 403, nerve fiber layer 405, outer plexiform layer 406, and the retinal pigment epithelium 407 shown in FIG. 4. FIG. 4 is a chart for explaining the relationship between the fundus picture, retinal volume data and the accumulated image.

As the fundus image capturing apparatus 4, an OCT capable of capturing the tomosynthesis of the fundus or a fundus camera capable of capturing the fundus can be given used. Both the Time Domain OCT (TD-OCT) and the Fourier Domain OCT (FD-OCT) can be used. While in FD-OCT, capable of high-speed capture (as a plurality of tomosynthesis can be obtained with one capturing operation) the retinal volume data can be reconstructed by sequentially apposing these tomosynthesis. The fundus image capturing apparatus 4 captures the fundus images of the examinees (patients) in response to the operation of the users (operators or doctors), and outputs the obtained fundus images to the image processing apparatus 1. Further, the image processing apparatus 1 may be connected to the database 2 for storing the fundus images obtained by the fundus image capturing apparatus 4, and the necessary fundus images may be obtained from the database. Connection to these apparatuses may be done by an interface such as USB or IEEE1394, etc., or via an external network such as the Internet.

Next, the functional structure of the image processing apparatus 1 according to the present embodiment will be described with reference to FIG. 5. FIG. 5 is a chart showing an example of the functional structure of the image processing apparatus 1 according to the present embodiment. In FIG. 5, the image processing apparatus 1 comprises a fundus image input unit 501, a layer extraction unit 502, a blood vessel area extraction unit 503, a distance calculation unit 504, a distance transfer function setting unit 505, a luminance transfer function setting unit 506, and a visualization unit 507. Next, the operation of each unit will be explained.

The fundus image input unit 501 selects and inputs the fundus images output from the fundus image capturing apparatus 4 or the fundus images stored in the database 2. FIG. 4 shows pattern diagrams of the retinal volume data 401 and the fundus picture 421 input as the fundus image. The fact that the inside of the retina is formed as the layer structure is well-known in the medical field. The coordinate system of the retina volume data 401 is defined such that the lateral direction of the retina tomosynthesis 402 (pattern diagrams) is the X axis, the longitudinal direction is the Z axis and the direction to which the retina tomosynthesis 402 is apposed is the Y axis. Further, the coordinate system of the fundus picture 421 is defined such that the lateral direction is the X axis and the longitudinal direction is the Y axis.

The layer extraction unit 502 extracts the nerve fiber layer 405, outer plexiform layer 406 and the retinal pigment epithelium 407 from the retinal volume data 401. The layer extraction unit 502 extracts internal limiting membrane 404, the lower end of the nerve layer 405, the upper end of the outer plexiform layer 406, the upper end of the retinal pigment epithelium 407, and the retina 403 defined from the internal limiting membrane 404 to the lower end of retinal pigment epithelium 407. All layers or one or plural layers may be selected for extraction. The layer boundary information indicating the boundary position of the extracted layers is output to the distance calculation unit 504.

The blood vessel area extraction unit 503 extracts the blood vessel area from the input fundus image. As shown in FIG. 6, the blood vessel area extraction unit 503 is composed of an accumulated image blood vessel area extraction unit 601, a fundus picture blood vessel area extraction unit 602 and a blood vessel alignment unit 603. The accumulated image blood vessel extraction unit 601 extracts the fundus blood vessel area 412 from the accumulated image 411 accumulating the luminance value of the voxel of the retina volume data 401 in the Z-axis direction. Further, when the fundus picture is input in the fundus image input unit 501, the fundus picture blood vessel area extraction unit 602 extracts the blood vessel area 422 from the fundus picture 421. The blood vessel alignment unit 603 aligns the coordinate system (x, y) of the fundus picture and the coordinates (x, y) of the accumulated image by using the blood vessel areas 412 and 422 when the fundus picture is input in the fundus image input unit 501.

As a result of this processing, the blood vessel area extraction unit 503 outputs the blood vessel area expressed by the coordinates (x, y) as the assembly of the voxel to the distance calculation unit 504, distance transfer function setting unit 505 and the luminance transfer function setting unit 506.

The distance calculation unit 504 first identifies one layer boundary from the layer boundary information and assumes the position of the boundary to be distance=0. For example, when the internal limiting membrane is identified by selection, the distances of all voxels on the layer boundary extracted as the internal limiting membrane 404 shown in FIG. 4 are made to be 0. Next, the distance calculation unit 504 defines the blood vessel projection area 408, which is the assembly of the voxels having the coordinates (x, y) of the retinal volume data, by using the blood vessel area 412 which is the assembly of the voxels expressed by the coordinates (x, y) obtained by the blood vessel area extraction unit 503. Further, the distance calculation unit 504 calculates the distance between the respective voxels in the blood vessel projection area 408 and the reference point 409 existing at the crossing point of the layer boundary and the blood vessel projection area 408, and supplies the calculated distance to the respective voxels. In this case, it is assumed that the sign value of the distance of the voxel having a Z-axis value larger than that of the reference point 409 is "−", and the sign value of the distance of the voxel having the a Z-axis value smaller than that of the reference point 409 is "+".

Figure 1:
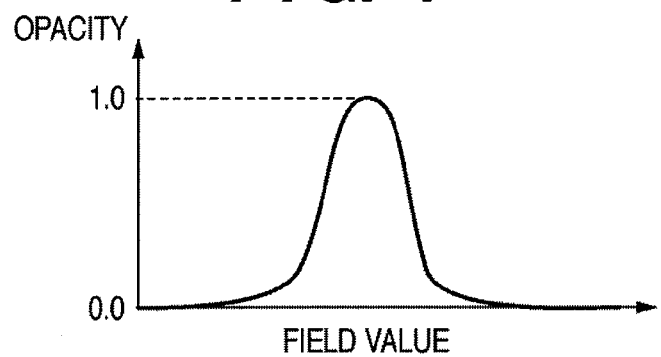
FIG. 1 is a chart showing an example of a transfer function for volume rendering.

The distance transfer function setting unit 505 sets the distance transfer function for converting the calculated distance of the respective voxels to the opacity by the distance calculation unit 504. The distance transfer function is the function defining distance in the lateral axis and opacity in the longitudinal axis, as shown in FIG. 1, and is automatically set depending on the subject of the display, such as a blood vessel or achromoderma. The distance transfer function setting unit 505 sets the distance from the reference point 409 to the fundus blood vessel 202 in which the fundus blood vessel is considered to run as the peak position of the distance transfer function, in the blood vessel projection area 408 extracted by the blood vessel area extraction unit 503.

Figure 2:
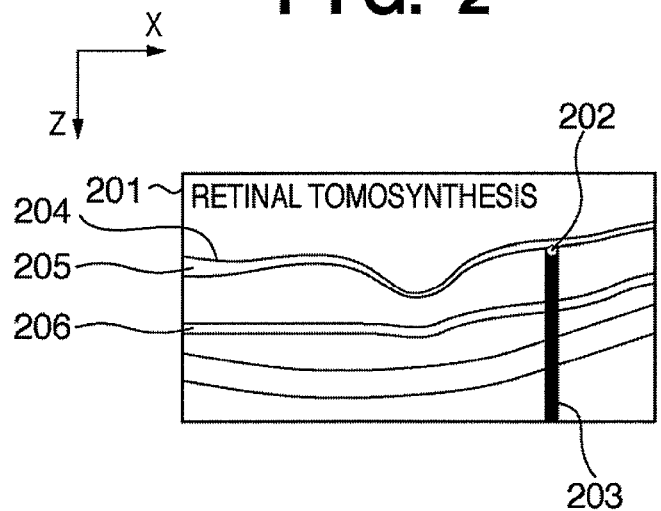
FIG. 2 is a chart for explaining a retinal tomosynthesis.

Here, the position in which the fundus blood vessel 202 is considered to run strongly reflects light, and the luminance value of the shadowed area 203 of the blood vessel in FIG. 2 is low relative to the peripheral area. Therefore, the position of the blood vessel is determined in the blood vessel projection area 408 to be the z value of the voxel having the maximum luminance value or the voxel having a large variance value in the rectangle when a rectangle of arbitrary size is assumed. The variance value of the distance transfer function can also be set from the diameter of the blood vessel, which can be calculated from the blood vessel area. The distance transfer function thus automatically set is output to the visualization unit 507.

The luminance transfer function setting unit 506 sets the luminance transfer function for converting the luminance value of the retinal volume data to opacity. The luminance transfer function is the function defining luminance value in the lateral axis and opacity in the longitudinal axis, for example, in FIG. 1. Setting of this function may be manually executed by the user using the user interface or executed automatically from the histogram of the luminance value as shown in the patent publication 3. The set luminance transfer function is output to the visualization unit 507.

The visualization unit 507 synthesizes the opacity calculated by the luminance transfer function and the opacity calculated by the distance transfer function by the formula 1 below, and the synthesized value is used to set the opacity of the voxel in the volume rendering operation. Here, it is assumed that the luminance value of the voxel in the x-coordinate is v(x), the distance is d(x), the luminance transfer function is $f_v(v(x))$, and the distance transfer function is $f_d(d(x))$. The synthesized opacity $\alpha$ (v(x), d(x)) is obtained by a linear sum of the luminance transfer function and the distance transfer function by using the synthesizing ratio $\beta$ of the luminance transfer function and the distance transfer function as shown in the formula 1.

$$\alpha(v(x),d(x))=\beta*f_v(v(x))+(1-\beta)*f_d(d(x)) \qquad \text{(Formula 1)}$$

$\beta$ may be set in advance for each subject of display. When the blood vessel is visualized, because the contrast in the vicinity of the blood vessel is low, $\beta$ can be set to be low and the weight of the distance transfer function can be large. Finally, the visualization unit 507 generates the translucent image as the resultant image of the volume rendering operation.

Figure 8:
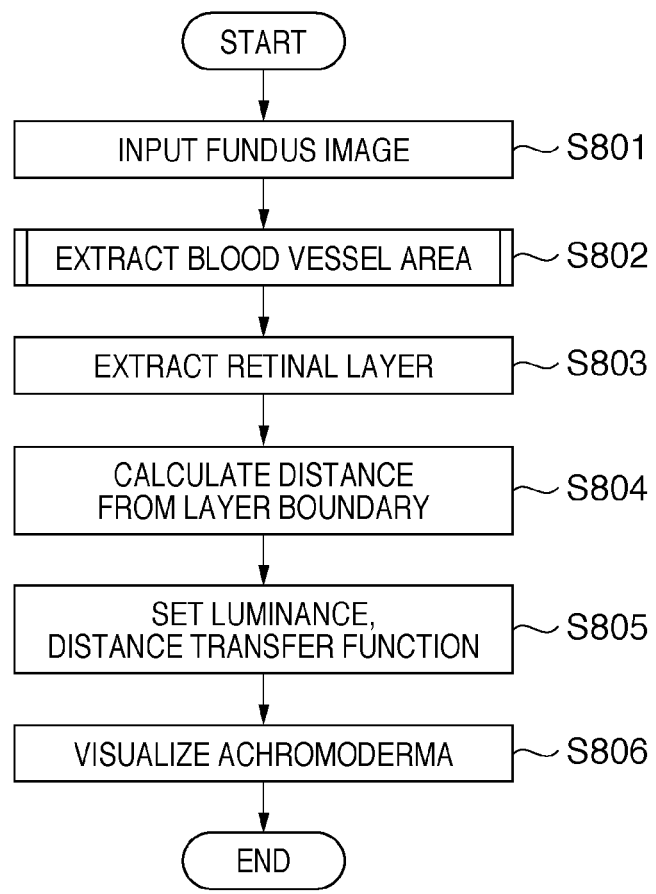
FIG. 8 is a flowchart showing the process flow to visualize the three-dimensional flow in the fundus blood vessel by volume rendering in the image processing apparatus 1 according to the first embodiment of the present invention.
Figure 12:
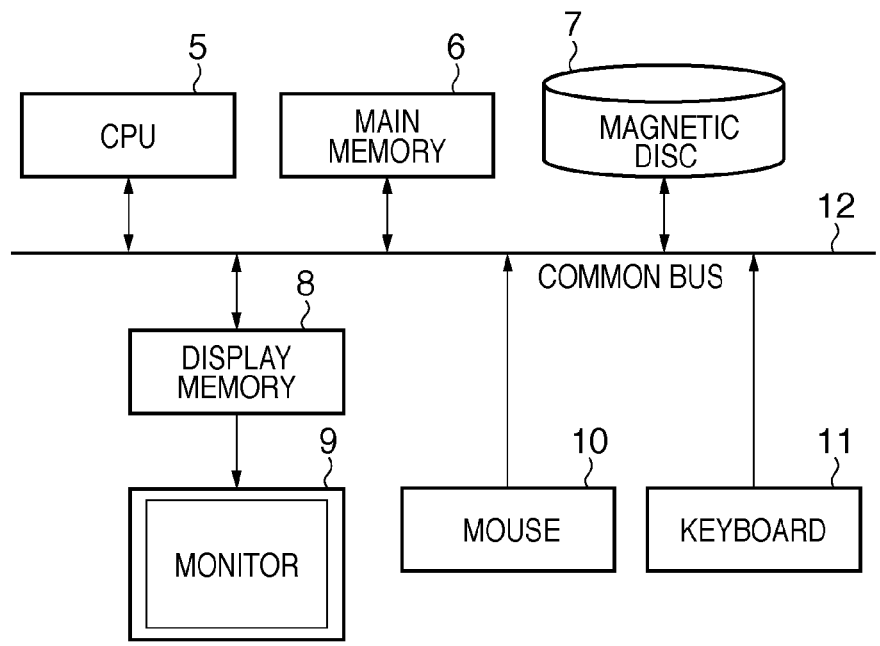
FIG. 12 is a chart showing a hardware structure of the image processing apparatus according to the embodiment of the present invention.

Next, the process flow to visualize the three-dimensional running of the fundus blood vessel in the image processing apparatus 1 according to the present embodiment will be explained with reference to the flowchart shown in FIG. 8. Here, the processing shown in the flowchart of FIG. 8 is realized by executing the program stored in the main memory 6 by the CPU 5, as shown in FIG. 12.

In step S801, the fundus image input unit 501 inputs the fundus image such as the retina volume data or fundus picture to the image processing apparatus 1. The input fundus image is output to the layer extraction unit 502, the blood vessel area extraction unit 503, the distance transfer function setting unit 505, the luminance transfer function setting unit 506 and the visualization unit 507.

In step S802, the blood vessel area extraction unit 503 extracts the blood vessel areas 412 and 422 from the retina volume data and the fundus image. The processing in this step will be described in more detail later with reference to FIG. 9.

In step S803, the layer extraction unit 502 extracts the nerve fiber layer 405, the outer plexiform layer 406 and the retinal pigment epithelium 407 from the retinal volume data received in step S801. The layer extraction unit 502 searches the internal limiting membrane 404, the lower end of the nerve fiber layer 405, the upper end of the outer plexiform layer 406, and the retina 403 from this layer information. By a instructing unit, not shown, the user selects the layer boundary as the reference and the layer boundary information is output to step S804.

In step S804, the distance calculation unit 504 calculates the distance from the layer boundary as the reference to the voxels existing in the z-axis direction in the blood vessel area extracted in step S802. The calculated distance information is output to the visualization unit 507. When the distance to the voxels outside the blood vessel area is not calculated, that is, the distance is 0, the opacity of the voxels outside the blood vessel area becomes 0 and volume rendering can be done at high speed. Further, when the distance to the voxels outside the blood vessel area is calculated as well, the translucent image can be generated by volume rendering while calculating the opacity in accordance with the distance from the layer.

In step S805, the luminance transfer function setting unit 506 and the distance transfer function setting unit 505 set the luminance transfer function and the distance transfer function, respectively. The distance transfer function setting unit 505 extracts the shadowed area of the blood vessel and considers the distance from the internal limiting membrane to the coordinates of the predetermined position where the blood vessel is considered to be running as the peak distance. The set luminance transfer function and the distance transfer function are output to the visualization unit 507.

In step S806, the visualization unit 507 executes the volume rendering while multiplying the opacity obtained from the luminance transfer function and the distance transfer function according to the formula 1.

Figure 9:
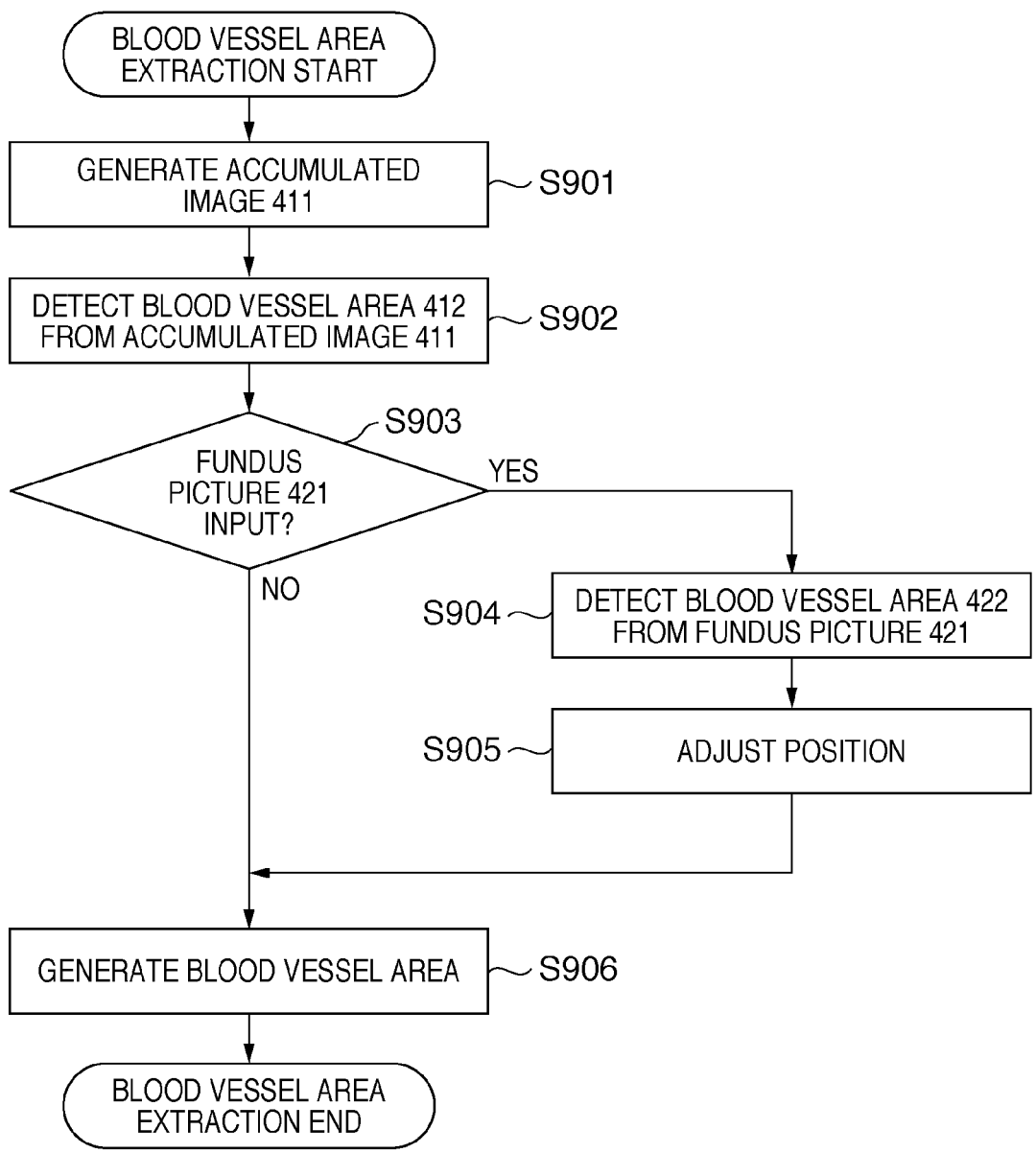
FIG. 9 is a flowchart showing the detailed operation of the extraction of the blood vessel area by the blood vessel area extraction unit 503 according to the first embodiment of the present invention.

FIG. 9 is a flowchart describing the processing in step S802. First, in step S901, the accumulated image blood vessel area extraction unit 601 generates the accumulated image 411 of the input retinal volume data 401. Further, the accumulated image blood vessel area extraction unit 601 extracts the blood vessel area 412 from the accumulated image 411 in step S902 and outputs it to the blood vessel alignment unit 603.

Here, as the method of extracting the blood vessel area 412 in step S902, an arbitrary known method can be used. For example, by analyzing the pixel value of the accumulated image, calculating the difference between the values of the adjacent pixels and searching the adjacent pixels in which the difference is greater than the predetermined value, the boundary area between the blood vessel area and the other area is detected. By this operation, the blood vessel area 412 can be extracted from the accumulated image. In the extracting process, the difference of the values of the pixels (such as the luminance value) of the blood vessel area and other area in the accumulated image is used.

In step S903, the fundus image input unit 501 judges whether the fundus picture 421 is input in step S801. If the fundus picture 421 is input ("YES" in step S903), the process moves to step S904. If the fundus picture 421 is not input ("NO" in step S903), the process moves to step S906.

In step S904, the fundus picture blood vessel area extraction unit 602 extracts the blood vessel area 422 from the fundus picture 421 and outputs the same to the blood vessel alignment unit 603. The method of extracting the blood vessel area 422 in step S903 is the same as that in step S902. That is, by analyzing the pixel value of the fundus picture 421, calculating the difference between the values of adjacent pixels and searching the adjacent pixel in which the difference is greater than the predetermined value, the boundary area between the blood vessel area and other area is detected. By this operation, the blood vessel area 412 can be extracted from the accumulated image. In step S905, the blood vessel alignment unit 603 aligns the blood vessel areas 412 and 422 such that the positions are in accord with each other.

In the subsequent step S906, the blood vessel alignment unit 603 consolidates the blood vessel area 412 of the fundus picture 421 and the blood vessel area 422 of the accumulated image 411, and the consolidated blood vessel area is supplied to step S803. Combining of the blood vessel area 412 and the blood vessel area 422 may be done by a logical multiplication or logical summation of them. If the fundus picture 421 is not available, the blood vessel area 412 extracted from the accumulated image 411 is supplied to step S803. Here, step S802 is complete.

As described above, in the present embodiment, the knowledge that the fundus blood vessel runs through the vicinity of the lower end of the nerve fiber layer is expressed by the distance transfer function, and the feature that the luminance value of the fundus blood vessel in the retinal tomosynthesis is high is expressed by the luminance transfer function, and the volume rendering operation is executed. As a result of that, the three-dimensional rendering of the fundus blood vessel in the retinal volume data can be visualized.

Second Embodiment

Visualizing the Achromoderma

In the above first embodiment, the three-dimensional rendering of the fundus blood vessel is visualized by extracting the blood vessel area and the layer boundary from the fundus image, and by volume-rendering the blood vessel using the opacity calculated from the distance from the layer boundary and the luminance value of the retinal volume data. On the other hand, in the second embodiment, not the blood vessel but the achromoderma is visualized as the discriminative lesion of the fundus oculi.

Figure 10:
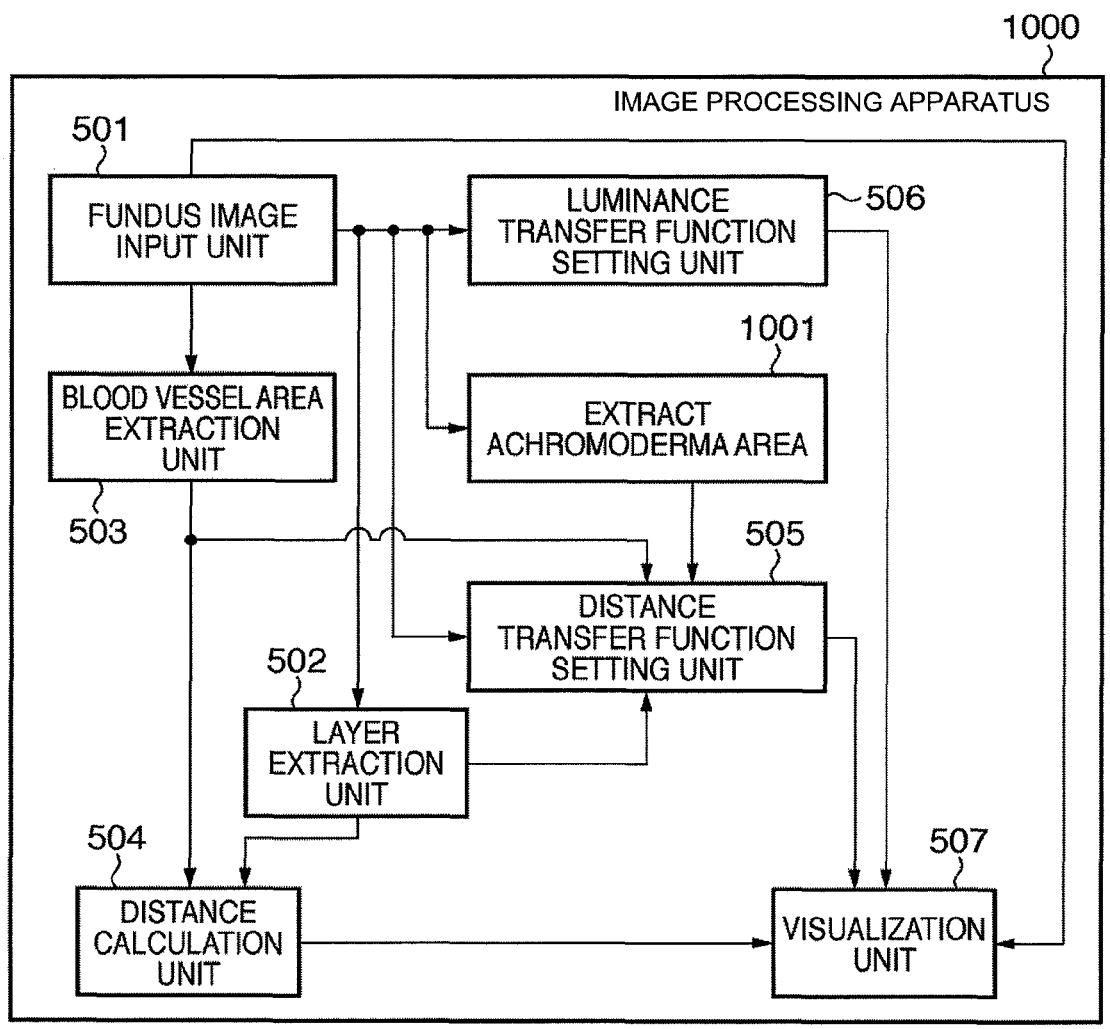
FIG. 10 is a chart showing one example of the functional structure of the image processing apparatus 1000 according to the second embodiment of the present invention.

The structure of the image processing apparatus and the apparatus connected thereto is same as that of the first embodiment as shown in FIG. 2. However, the functional block of the image processing apparatus according to the present embodiment is configured by adding an achromoderema area extraction unit 1001 to the functional block according to the first embodiment as shown in FIG. 10.

The description of this embodiment will primarily explain the achromoderma area extraction unit 1001 and an achromoderema center searching unit 704 (one functional block of the distance transfer function setting unit 505). The explanation of other functional blocks is abbreviated, as they process similar to those of the first embodiment.

The achromoderma area extraction unit 1001 extracts the achromoderma area from the input fundus image. When the input fundus image is retinal volume data 401, the achromoderma area is extracted based on the retinal layer information and the luminance value. Here, the achromoderma area can be predicted from the medical knowledge that the position where the achromoderma appears is near the outer plexiform layer 406. In order to use this medical knowledge, the nerve fiber layer 405 and retinal pigment epithelium 407 are extracted first. Further, because the achromoderma in the retinal tomosynthesis 402 has a high luminance value compared with that of the surrounding area, the area having the high luminance value between the nerve fiber layer 405 and the retinal pigment epithelium 407 is extracted by the image processing, such as binary processing, and is determined as the achromoderma area of the retinal volume data 401.

When a fundus picture 421 other than the retinal volume data 401 is input, as there are cases in which the fundus picture 421 can better grasp the achromoderma, the two-dimensional achromoderma area is first extracted in the fundus picture 421. The extracting method herein can be realized by image processing, such as binary processing, by using the fact that the achromoderma has a high luminance value compared with that of the surrounding area.

Next, based on the alignment information calculated in the blood vessel area extraction unit 503, the achromoderma projection area similar to the blood vessel projecting area is searched by reverse projecting the achromoderma area to the retinal volume data 401 in the fundus picture 421. Further, as described above, an achromoderma area is extracted from the voxels in the achromoderma projection area. By this method, it is possible to include an achromoderma not appearing in the retinal volume data 401 but appearing in the fundus picture 421.

The achromoderma center searching unit 704 in the distance transfer function setting unit 505 searches the voxels in the achromoderma area extracted by the achromoderma area extraction unit 1001 in the z-axis direction. In this case, one layer boundary is selected from the layer boundary information and the distance from the selected layer boundary (for example, the internal limiting membrane 404) to the voxels existing in the center of the achromoderma area is calculated and defined as the peak position of the distance transfer function.

Figure 11:
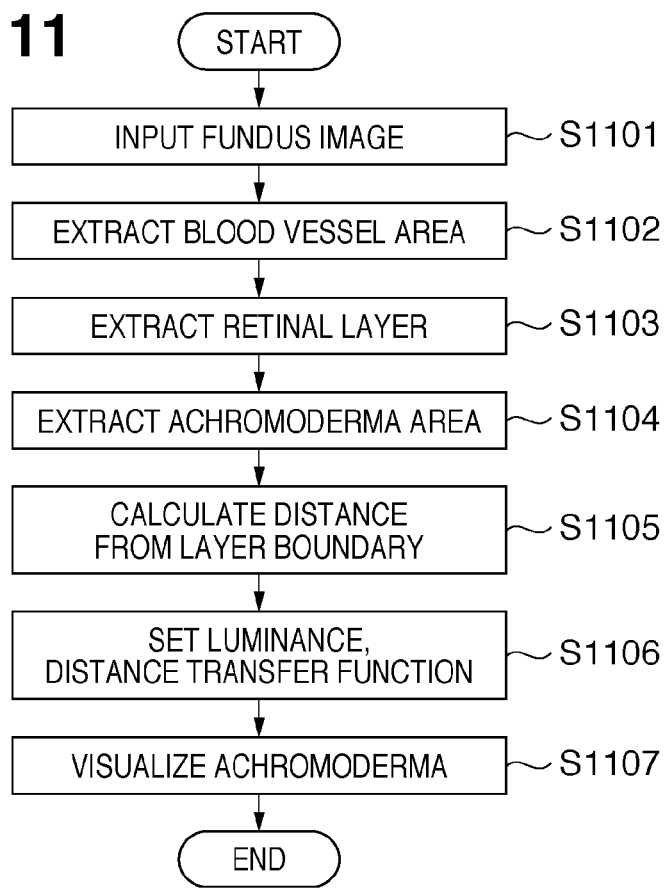
FIG. 11 is a flowchart showing a process flow to visualize the achromoderma of the retinal volume data in the image processing apparatus 1000.

Next, the process flow to visualize the achromoderma of the retinal volume data will be explained with reference to the flowchart shown in FIG. 11. Here, the processing shown by the flowchart of FIG. 11 is realized by executing the program stored in the main memory 6 by the CPU 5. As the steps S1101, S1102, S1103, S1105, and S1107 are the same as the steps S801, S802, S803, S804, and S806 in FIG. 8, respectively, an explanation of these steps will be abbreviated.

In step S1104, when the input fundus image is only retinal volume data 401, the three-dimensional achromoderma area is extracted from the retinal volume data 401. When the fundus picture 421 in addition to the retinal volume data 401 is also input, first, the achromoderma area is extracted from the fundus picture 421. Next, based on the blood vessel alignment information calculated in the blood vessel alignment unit 603, the achromoderma area of the fundus picture 421 is reverse projected to the retinal volume data 401. Further, the three-dimensional area of the achromoderma is extracted by using the layer information extracted in step S1103. The information of the extracted achromoderma is output to the distance calculation unit 504.

In step S1106, the luminance transfer function setting unit 506 and the distance transfer function setting unit 505 set the luminance transfer function and the distance transfer function respectively. The distance transfer function setting unit 505 searches the predetermined position corresponding to the center of the extracted achromoderma area. The predetermined positions on z-axis of the achromoderma area from the internal limiting membrane 404 are determined as the peak positions of the distance transfer function. The set luminance transfer function and the distance transfer function are output to the visualization unit 507.

As described above, in the second embodiment, the knowledge that the achromoderma appears in the vicinity of the outer plexiform layer is expressed by the distance transfer function, and the feature that the luminance value of the achromoderma is high in the retinal tomosynthesis is expressed by the luminance transfer function, and the volume rendering is executed. By this operation, the three dimensional distribution of the achromoderma of the retinal volume data can be visualized.

Third Embodiment

The image processing apparatus and the apparatus connected thereto are same as those of the first embodiment, as shown in FIG. 2. The basic structure of the computer for realizing the function of the respective units is also same as that of the first embodiment, as shown in FIG. 12.

Figure 7:
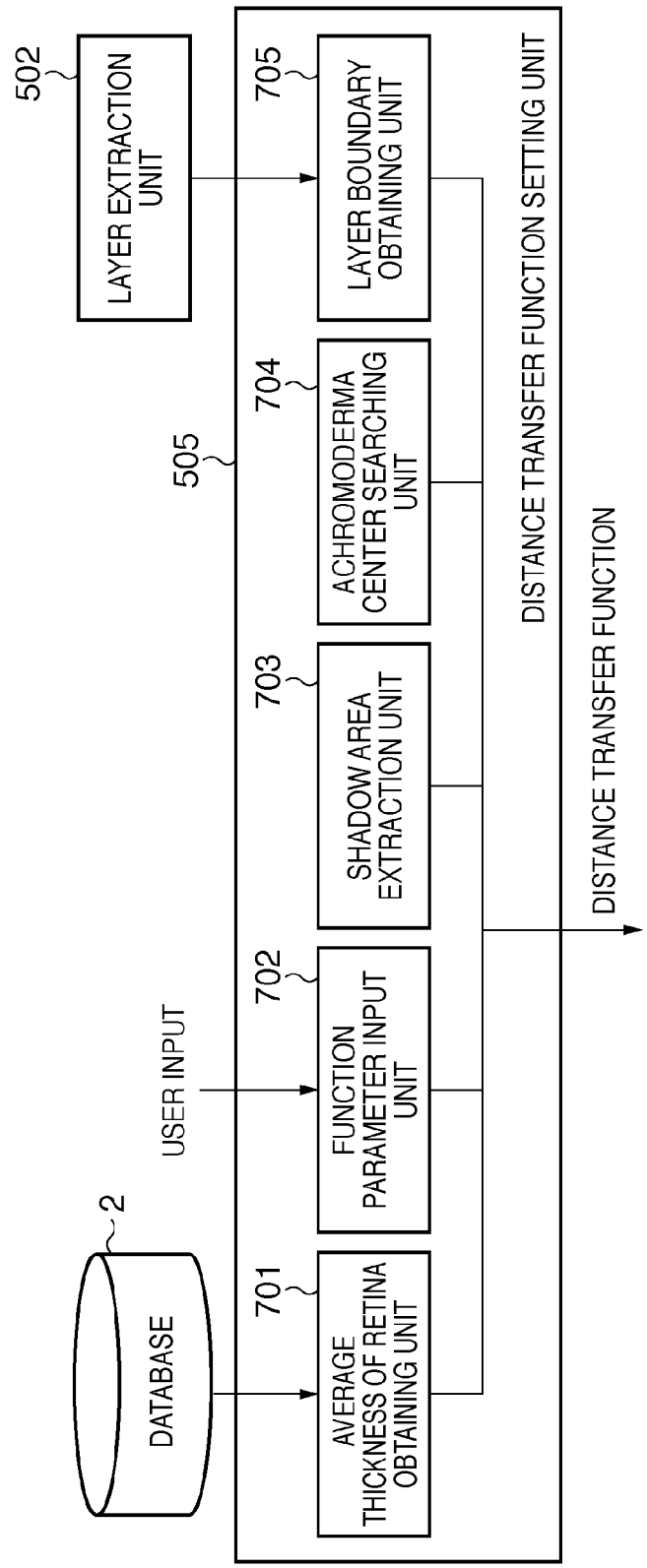
FIG. 7 is a chart showing one example of the functional structure of a distance transfer function setting unit 505 according to an embodiment of the present invention.

The distance transfer function setting unit 505 in the first and second embodiments comprises an average thickness of the retina obtaining unit 701, function parameter input unit 702, a shadow area extraction unit 703, the achromoderma center searching unit 704 and a layer boundary obtaining unit 705, as shown in FIG. 7. The distance transfer function is set by using the shadowed area extraction unit 703 in the first embodiment and by using the achromoderma center searching unit 704 in the second embodiment. In the present embodiment, the method of setting the distance transfer function by using one of the average thickness of the retina obtaining unit 701, the function parameter input unit 702 and the layer boundary obtaining unit 705 will be described.

The average thickness of the retina obtaining unit 701 obtains the average thickness of the respective layers from the database 2, and based on the obtained thickness, the predetermined position corresponding to the peak position of the distance transfer function is determined. When the fundus blood vessel is visualized, as the fundus blood vessel appears in the vicinity of the lower end of the nerve fiber layer, the average thickness of the nerve fiber layer is obtained. When the achromoderma is visualized, as the achromoderma appears in the vicinity of the outer plexiform layer 406, the average thickness from the internal limiting membrane 404 to the upper end of the outer plexiform layer 406 is obtained. The predetermined position having the obtained thickness is determined as the peak position of the opacity, and the distance transfer function is set such that the opacity is 1.0.

The function parameter input unit 702 manually sets the peak position by using the user interface. The layer boundary obtaining unit 705 obtains the boundary information of the respective layers from the layer extraction unit 502 and sets the same as the peak position of the distance transfer function. When the fundus blood vessel is visualized, the boundary information of the nerve fiber layer is obtained and the peak position is set such that the thickness of the nerve fiber layer has an opacity equal to 1.0. When the achromoderma is visualized, the boundary information of the outer plexiform layer is obtained and the peak position is set such that the thickness from the internal limiting membrane to the outer plexiform layer has an opacity equal to 1.0.

As described above, the distance transfer function is set by using one of the average value of the retina obtaining unit 701, the function parameter input unit 702, the shadowed area extraction unit 703, the achromoderma center searching unit 704, and the layer boundary obtaining unit 705 forming the distance transfer function setting unit 505. By this operation, the three-dimensional rendering of the fundus blood vessel or the three-dimensional distribution of the achromoderma can be visualized.

Fourth Embodiment

Next, the basic structure of the computer for realizing the functions of the respective blocks of the image processing apparatus according to the first, second and third embodiments by computer program will be explained with reference to FIG. 12.

A CPU 5 controls the entire computer by using the data or the program stored in the main memory 6. The CPU 5 also controls the execution of the software corresponding to the respective units of the image processing apparatus 1, to realize the functions of the respective units.

The main memory 6 stores the control program executed by the CPU 5 or provides a working area when the program is executed.

The magnetic disc 7 stores various kinds of application software including an operating system (OS), peripheral device drive and program for displaying the fundus image. A display memory 8 temporarily stores display data for the monitor 9.

The monitor 9 is, for example, a CRT monitor or LCD monitor, and displays the image based on the data from the display memory 8. A mouse 10 and a key-board 11 execute pointing input and input of letters by the user, respectively. The user can supply various instructions to the image processing apparatus 1 by using them. The above respective elements are connected with each other by a common bus 12 such that they can communicate.

Other Embodiments

Aspects of the present can also be realized by a computer of a system or apparatus (or devices such as a CPU or MPU) that reads out and executes a program recorded on a memory device to perform the functions of the above described embodiments, and by a method, the steps of which are performed by a computer of a system or apparatus by, for example, reading out and executing a program recorded on a memory device to perform the functions of the above described embodiments. For this purpose, the program is provided to the computer for example via a network or from recording media of various types serving as the memory devices (e.g., computer-readable media).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The application claims the benefit of Japanese Patent Application No. 2008-324709 filed Dec. 19, 2008, which is hereby incorporated by reference herein in its entirety.

The invention claimed is:

1. An image processing apparatus comprising:
   an obtaining unit configured to obtain a position of a predetermined area in the retina tomographic image; and
   a visualizing unit configured to generate a translucent image by calculating the opacity of respective positions of the retina tomographic image in response to both a distance from the position of the predetermined area and a luminance value of the retina tomographic image, and by volume rendering.

2. The image processing apparatus according to claim 1, further comprising:
   a blood vessel area extracting unit configured to extract an area in which a fundus blood vessel exists in the retina of an examinee,
   wherein the predetermined area is the area in which the fundus blood vessel exists in the retina.

3. The image processing apparatus according to claim 2, wherein said blood vessel area extracting unit specifies a position of the fundus blood vessel in a fundus picture of an eye of the examinee, and extracts the area in which the fundus blood vessel exists in the retina using the specified position of the fundus blood vessel.

4. The image processing apparatus according to claim 1, further comprising:
   an achromoderma area extracting unit configured to extract an area in which an achromoderma exists in the retina of an examinee,
   wherein the predetermined area is the area in which an achromoderma exists in the retina.

5. The image processing apparatus according to claim 4, wherein said achromoderma area extracting unit specifies a position of the achromoderma area in a fundus picture of an eye of the examinee, and extracts the area in which the achromoderma exists in the retina using the specified position of the achromoderma.

6. The image processing apparatus according to claim 1, further comprising:
   a distance transfer function setting unit configured to set a distance transfer function for converting the distance from the position of the predetermined area to a parameter expressing opacity; and
   a luminance transfer function setting unit configured to set a luminance transfer function for converting a luminance value of a fundus image showing the retina tomographic image to the parameter expressing opacity,
   wherein said visualizing unit generates the translucent image by calculating the opacity of respective positions of the retina tomographic image using the distance transfer function and the luminance transfer function, and by volume rendering.

7. The image processing apparatus according to claim 6, wherein said distance transfer function setting unit converts, based on the distance from a specified boundary position in the retina, the distance to the parameter expressing opacity such that the predetermined area in the retina has the peak of opacity.

8. The image processing apparatus according to claim 7, further comprising:
   a database for storing the thickness of the respective layers forming the retinal layers,
   wherein said distance transfer function setting unit specifies a predetermined area in the retina based on the thickness of the respective layers and converts, based on the distance from the specified boundary position, the distance to the parameter expressing opacity such that the predetermined area has the peak of opacity.

9. The image processing apparatus according to claim 1, further comprising:
   a second obtaining unit configured to obtain predetermined boundary positions of retina layers in the retina tomographic image,
   wherein said visualizing unit generates the translucent image further based on the opacity in response to the distance between the boundary position and the position of the predetermined area.

10. The image processing apparatus according to claim 1, further comprising a display controller configured to display the created translucent image on a display unit.

11. A control method of an image processing apparatus, said method comprising steps of:
    obtaining a position of a predetermined area in the retina tomographic image; and
    visualizing and generating a translucent image by calculating the opacity of respective positions of the retina tomographic image in response to both a distance from the position of the predetermined area and a luminance value of the retina tomographic image, and by volume rendering.

12. A non-transitory computer-readable storage medium storing a computer program which causes a computer to perform a control method of an image processing apparatus, wherein the control method comprises:
    obtaining a position of a predetermined area in the retina tomographic image; and
    visualizing and generating a translucent image by calculating the opacity of respective positions of the retina tomographic image in response to both a distance from the position of the predetermined area and a luminance value of the retina tomographic image, and by volume rendering.

13. An image processing system comprising:
    an optical coherence tomography apparatus for capturing a tomographic image of an eye of an examinee; and
    an image processing apparatus comprising:
    (a) an obtaining unit configured to obtain a position of a predetermined area in the retina tomographic image; and
    (b) a visualizing unit configured to generate a translucent image by calculating the opacity of respective positions of the retina tomographic image in response to both a distance from the position of the predetermined area and a luminance value of the retina tomographic image, and by volume rendering.

14. An image processing apparatus comprising:
- a specifying unit configured to specifying one of boundary positions of retina layers in a fundus image showing a retina tomographic image;
- a distance transfer function setting unit configured to set a distance transfer function for converting the distance from the specified boundary position to a parameter expressing opacity such that the peak position of the opacity is set to a predetermined position in the retina;
- a luminance transfer function setting unit configured to set a luminance transfer function for converting a luminance value of the fundus image to the parameter expressing opacity; and
- a visualizing unit configured to generate a translucent display image by calculating the opacity of respective positions of the tomographic image using the distance transfer function and the luminance transfer function, and by volume rendering.

15. A control method of an image processing apparatus, the method comprising the steps of:
- specifying one of retinal layer boundary positions in a fundus image showing a retinal tomographic image;
- setting a distance transfer function for converting the distance from the specified boundary position to a parameter expressing opacity such that the peak position of the opacity is set to a predetermined position in the retina;
- setting a luminance transfer function for converting the luminance value of the fundus image to the parameter expressing opacity; and
- generating a translucent image by calculating the opacity of respective positions of the tomographic image using the distance transfer function and the luminance transfer function, and by volume rendering.

16. A computer program stored in a non-transitory computer-readable storage medium, which causes an image processing apparatus to perform a method comprising the steps of:
- specifying one of boundary positions of retina layers in a fundus image showing a retina tomographic image;
- setting a distance transfer function for converting the distance from the specified boundary position to a parameter expressing opacity such that the peak position of the opacity is set to a predetermined position in the retina;
- setting a luminance transfer function for converting a luminance value of the fundus image to the parameter expressing opacity; and
- generating a translucent display image by calculating the opacity of respective positions of the tomographic image using the distance transfer function and the luminance transfer function, and by volume rendering.

17. An ophthalmic apparatus comprising:
- an obtaining unit configured to obtain a three-dimensional tomographic image of an eye to be examined; and
- a generation unit configured to generate, based on a two-dimensional area within an integrated image of the three-dimensional tomographic image and a predetermined layer of the three-dimensional tomographic image, an image which visualizes a three-dimensional area within the three-dimensional tomographic image.

18. The ophthalmic apparatus according to claim 17, further comprising:
- a layer extraction unit configured to extract, as the predetermined layer, a nerve fiber layer of the eye to be examined from the three-dimensional tomographic image,
- wherein the generation unit generates, as the image which visualizes a three-dimensional area, an image which visualizes a three-dimensional running of blood vessel based on (a) the extracted nerve fiber layer and (b) the two-dimensional area.

19. The ophthalmic apparatus according to claim 18, further comprising:
- a blood vessel area extraction unit configured to extract, as the two-dimensional area, a two-dimensional blood vessel area from the integrated image; and
- a determination unit configured to determine a position of the three-dimensional running of blood vessel as the three-dimensional area in a depth direction, based on a position of the extracted nerve fiber layer within the three-dimensional tomographic image,
- wherein the generation unit generates the image which visualizes the three-dimensional running of blood vessel based on (a) the determined position and (b) a position of the extracted two-dimensional blood vessel area.

20. The ophthalmic apparatus according to claim 19, wherein the determination unit determines, based on an opacity of the three-dimensional tomographic image corresponding to a direction from a first position of the three-dimensional tomographic image in the depth direction of the eye to be examined, a second position of the three-dimensional tomographic image as the position of the two-dimensional area in the depth direction.

21. The ophthalmic apparatus according to claim 19, wherein the determination unit determines a position around a lower end of the nerve fiber layer as the position of the three-dimensional running of blood vessel in the depth direction.

22. The ophthalmic apparatus according to claim 17, wherein the generation unit generates the image in which at least a portion within the three-dimensional area has a peak position.

23. The ophthalmic apparatus according to claim 18, wherein the generation unit generates the image which visualizes the three-dimensional running of blood vessel based on (a) a function of an opacity of the three-dimensional tomographic image corresponding to a distance from the predetermined position in the three-dimensional tomographic image in the depth direction of the eye to be examined, (b) a distance from the predetermined position to the predetermined layer, and (c) a position of the two-dimensional area within the three-dimensional tomographic image, the two-dimensional area being a two-dimensional blood vessel area.

24. A control method of an ophthalmic apparatus, the method comprising the steps of:
- obtaining a three-dimensional tomographic image of an eye to be examined; and
- generating, based on a two-dimensional area within an integrated image of the three-dimensional tomographic image and a predetermined layer of the three-dimensional tomographic image, an image which visualizes a three-dimensional area within the three-dimensional tomographic image.

25. The control method of an ophthalmic apparatus according to claim 24, the method further comprising a step of:
- extracting, as the predetermined layer, a nerve fiber layer of the eye to be examined from the three-dimensional tomographic image,
- wherein in the generating step, as the image which visualizes a three-dimensional area, an image which visualizes a three-dimensional running of blood vessel is generated based on (a) the extracted nerve fiber layer and (b) the two-dimensional area.

26. The method according to claim 25, further comprising the steps of:
- extracting, as the two-dimensional area, a two-dimensional blood vessel area from the integrated image; and
- determining a position of the three-dimensional running of blood vessel as the three-dimensional area in a depth direction, based on a position of the extracted nerve fiber layer of the three-dimensional tomographic image,
- wherein in the generating step, the image which visualizes the three-dimensional running of blood vessel is generated based on the determined position and a position of the extracted two-dimensional blood vessel area.

27. The control method of an ophthalmic apparatus according to claim 25, wherein in the generating step, the image which visualizes the three-dimensional running of blood vessel is generated based on (a) a function of an opacity of the three-dimensional tomographic image corresponding to a distance from the predetermined position in the three-dimensional tomographic image in the depth direction of the eye to be examined, (b) a distance from the predetermined position to the predetermined layer, and (c) a position of the two-dimensional area in the three-dimensional tomographic image, the two-dimensional area being a two-dimensional blood vessel area.

28. A computer program stored in a non-transitory computer-readable storage medium, which causes an ophthalmic apparatus to perform a method comprising the steps of:
- obtaining three-dimensional tomographic image of an eye to be examined; and
- generating, based on a two-dimensional area within an integrated image of the three-dimensional tomographic image and a predetermined layer of the three-dimensional tomographic image, an image which visualizes a three-dimensional area within the three-dimensional tomographic image.

29. An image processing apparatus configured to create a translucent image of an object tomographic image, the image processing apparatus comprising:
- an obtaining unit configured to obtain a position of a predetermined area in the object tomographic image; and
- a creating unit configured to create the translucent image by making the object tomographic image opaque based on the position of the predetermined area.

30. A control method of an image processing apparatus configured to create a translucent image of an object tomographic image, said method comprising:
- an obtaining step of obtaining a position of a predetermined area in the object tomographic image; and
- a creating step of creating the translucent image by making the object tomographic image opaque based on the position of the predetermined area.

31. A computer program stored in a non-transitory computer-readable storage medium, which causes a computer to function as an image processing apparatus for creating a translucent image of an object tomographic image, the image processing apparatus comprising:
- an obtaining unit configured to obtain a position of a predetermined area in the object tomographic image; and
- a creating unit configured to create the translucent image by making the object tomographic image opaque based on the position of the predetermined area.

32. An ophthalmic apparatus comprising:
- an obtaining unit configured to obtain a three-dimensional tomographic image of an eye to be examined and a two-dimensional fundus image of the eye to be examined corresponding to the three-dimensional tomographic image; and
- a generation unit configured to generate, based on a predetermined layer within the three-dimensional tomographic image and a two-dimensional lesion area within the two-dimensional fundus image, an image which visualizes a three-dimensional lesion area within the three-dimensional tomographic image.

33. The ophthalmic apparatus according to claim 32, further comprising:
- a white patch area extraction unit configured to extract, as the two-dimensional lesion area, a two-dimensional white patch area of the eye to be examined from the two-dimensional fundus image,
- wherein the generation unit generates, as the image which visualizes a three-dimensional lesion area, an image which visualizes a three-dimensional white patch area, based on (a) the predetermined layer and (b) the extracted two-dimensional white patch area.

34. The ophthalmic apparatus according to claim 33, further comprising:
- a layer extraction unit configured to extract, as the predetermined layer, an outer plexiform layer of the eye to be examined from the three-dimensional tomographic image; and
- a determination unit configured to determine a position of the three-dimensional white patch area in a depth direction within the three-dimensional tomographic image, based on a position of the extracted outer plexiform layer within the three-dimensional tomographic image,
- wherein the generation unit generates the image which visualizes the three-dimensional white patch area based on the determined position and a position of the extracted two-dimensional white patch area within the three-dimensional tomographic image.

35. The ophthalmic apparatus according to claim 34, wherein the determination unit determines a position around the extracted outer plexiform layer as the position of the three-dimensional white patch area in the depth direction.

36. The ophthalmic apparatus according to claim 35, wherein the two-dimensional fundus image is a fundus picture of the eye to be examined corresponding to the three-dimensional tomographic image, and
wherein the white patch area extraction unit extracts the white patch area from the fundus picture.

37. The ophthalmic apparatus according to claim 33, wherein the two-dimensional fundus image is a fundus picture of the eye to be examined corresponding to the three-dimensional tomographic image, and
wherein the white patch area extraction unit extracts the two-dimensional white patch area from the fundus picture.

38. The ophthalmic apparatus according to claim 32, wherein the generation unit generates, as the image which visualizes a three-dimensional lesion area, an image which visualizes the three-dimensional white patch area, based on (a) a function of an opacity of the three-dimensional tomographic image corresponding to a distance from the predetermined position in the three-dimensional tomographic image in the depth direction, (b) a distance from the predetermined position to the predetermined layer, and (c) a position of the two-dimensional area within the three-dimensional tomographic image, the two-dimensional area being a two-dimensional white patch area.

39. A control method of an ophthalmic apparatus, the method comprising the steps of:
- obtaining a three-dimensional tomographic image of an eye to be examined and a two-dimensional fundus image of the eye to be examined corresponding to the three-dimensional tomographic image; and generating, based on a predetermined layer within the three-dimensional tomographic image and a two-dimensional lesion area within the two-dimensional fundus image, an image which visualizes a three-dimensional lesion area within the three-dimensional tomographic image.

40. The control method of an ophthalmic apparatus according to claim 30, further comprising the step of:

extracting, as the two-dimensional lesion area, a two-dimensional white patch area of the eye to be examined from the two-dimensional fundus image, wherein in the generating step, as the image which visualizes a three-dimensional lesion area, an image which visualizes a three-dimensional white patch area is generated, based on (a) the predetermined layer and (b) the extracted two-dimensional white patch area.

41. The control method of an ophthalmic apparatus according to claim 40, wherein the two-dimensional fundus image is a fundus picture of the eye to be examined corresponding to the three-dimensional tomographic image, and wherein in the extracting step, the two-dimensional white patch area is extracted from the fundus picture.

42. The control method of an ophthalmic apparatus according to claim 40, further comprising the steps of:

extracting, as the predetermined layer, an outer plexiform layer of the eye to be examined from the three-dimensional tomographic image; and determining a position of the three-dimensional white patch area in a depth direction within the three-dimensional tomographic image, based on a position of the extracted outer plexiform layer within the three-dimensional tomographic image, wherein in the generating step, the image which visualizes the three-dimensional white patch area is generated based on the determined position and a position of the extracted two-dimensional white patch area within the three-dimensional tomographic image.

43. The control method of an ophthalmic apparatus according to claim 39, wherein in the generating step, as the image which visualizes a three-dimensional lesion area, an image which visualizes the three-dimensional white patch area is generated, based on (a) a function of an opacity of the three-dimensional tomographic image corresponding to a distance from the predetermined position in the three-dimensional tomographic image in the depth direction, (b) a distance from the predetermined position to the predetermined layer, and (c) a position of the two-dimensional area within the three-dimensional tomographic image, the two-dimensional area being a two-dimensional white patch area.

44. A computer program stored in a non-transitory computer-readable storage medium, which program causes an ophthalmic apparatus to perform a method comprising the steps of:

obtaining a three-dimensional tomographic image of an eye to be examined and a two-dimensional fundus image of the eye to be examined corresponding to the three-dimensional tomographic image; and generating, based on a predetermined layer within the three-dimensional tomographic image and a two-dimensional lesion area within the two-dimensional fundus image, an image which visualizes a three-dimensional lesion area within the three-dimensional tomographic image.

* * * * *